United States Patent
Falck, Jr. et al.

(10) Patent No.: US 11,224,343 B2
(45) Date of Patent: Jan. 18, 2022

(54) REPLACEABLE PRISM WITH FLEXIBLE TAB SYSTEM FOR APPLANATION TONOMETER, APPLANATION TONOMETER CONTAINING SAME, AND METHOD OF LOADING PRISM INTO APPLANATION TONOMETER

(71) Applicant: Falck Medical, Inc., Mystic, CT (US)

(72) Inventors: Francis Y. Falck, Jr., Stonington, CT (US); Robert Falck, Stonington, CT (US)

(73) Assignee: FALCK MEDICAL, INC., Mystic, CT (US)

( * ) Notice: Subject to any disclaimer, the term of this patent is extended or adjusted under 35 U.S.C. 154(b) by 0 days.

(21) Appl. No.: 17/058,025

(22) PCT Filed: May 21, 2019

(86) PCT No.: PCT/US2019/033333
§ 371 (c)(1),
(2) Date: Nov. 23, 2020

(87) PCT Pub. No.: WO2019/226662
PCT Pub. Date: Nov. 28, 2019

(65) Prior Publication Data
US 2021/0204810 A1     Jul. 8, 2021

Related U.S. Application Data

(60) Provisional application No. 62/674,768, filed on May 22, 2018.

(51) Int. Cl.
*A61B 3/16*     (2006.01)
*G02B 7/18*     (2021.01)

(52) U.S. Cl.
CPC .............. *A61B 3/16* (2013.01); *G02B 7/1805* (2013.01)

(58) Field of Classification Search
CPC ..... A61B 3/0025; A61B 3/103; A61B 3/1015; A61B 3/14; A61B 3/10; A61B 3/1005;
(Continued)

(56) References Cited

U.S. PATENT DOCUMENTS 3,767,293 A     10/1973    Baker et al.
5,070,875 A     12/1991    Falck et al.
(Continued)

OTHER PUBLICATIONS

Britt, James M et al., "Microaerosol Formation in Noncontact 'Air-Puff' Tonometry", Archives of Ophthalmology, vol. 109, No. 2, pp. 225-228 (1991).
(Continued)

*Primary Examiner* — William R Alexander
*Assistant Examiner* — Sharrief I Broome
(74) *Attorney, Agent, or Firm* — Sheppard, Mullin, Richter & Hampton LLP (57) ABSTRACT

An optical prism mounting system is described that includes a prism having a flexible insertion tab system. Also described, is a prism holder having an insertion channel, and a method of mounting the prism in a tonometer. The flexible insertion tab system includes a spring tab and a bendable tab; the spring tab is flexed as the prism moves along the channel; the flexible insertion tab system connects with the prism holder and snaps into a locked position at the end of the channel; and the prism and the prism holder can be separated after use by disengaging the flexible insertion tab system. An optical operating range of the optical prism is from about 0 ADC to about 600 ADC, and the maximum time for setting the tonometer is not more than about 150 seconds.

34 Claims, 3 Drawing Sheets

(58) Field of Classification Search
CPC ........... A61B 3/102; A61B 3/107; A61B 3/12;
A61B 3/0091; A61B 3/112; A61B 3/152;
A61B 3/18; A61B 3/0008; A61B 3/0041;
A61B 3/0075; A61B 3/0083; A61B
3/0033; A61B 3/0058; A61B 3/1035;
A61F 2/16; A61F 2009/00872; A61F
2009/0088; A61F 9/008; A61F 2240/002;
A61F 9/00736; A61F 9/00804; A61F
2009/00848; A61F 2009/00897; A61F
2250/0002; A61F 2/1613; A61F 2/1624;
A61F 2009/00846; A61F 2009/0087;
A61F 2009/00882; A61F 2009/00887;
A61F 2009/00895; A61F 2/1637; A61F
2/164; A61F 9/007; G02C 7/027; G02C
7/028; G02C 7/04; G02C 7/083; G02C
11/10; G02C 2202/22; G02C 7/02; G02C
7/024; G02C 7/041; G02C 7/081; G02C
13/005; G02C 2202/10; G02C 2202/16;
G02C 2202/24; G02C 3/02; G02C 7/022;
G02C 7/025; G02C 7/047; G02C 7/06;
G02C 7/061; G02B 13/0095; G02B
17/0896; G02B 21/241; G02B 2027/0127;
G02B 2027/014; G02B 2027/0178; G02B
21/22; G02B 26/0841; G02B 26/101;
G02B 26/105; G02B 27/0018; G02B
27/0025; G02B 27/0075; G02B 27/017;
G02B 27/141; G02B 27/48; G02B
3/0006; G02B 7/023; G02B 9/12; G02B
9/14

See application file for complete search history.

(56) References Cited

U.S. PATENT DOCUMENTS

| | | | | |
|---|---|---|---|---|
| 5,305,747 | A | * | 4/1994 | McNaughton ........... A61B 3/16 359/837 |
| 6,736,778 | B2 | | 5/2004 | Falck, Jr. et al. |
| 2001/0002430 | A1 | | 5/2001 | Falck et al. |
| 2001/0051770 | A1 | * | 12/2001 | Falck, Jr. .................. A61B 3/16 600/398 |
| 2006/0217611 | A1 | * | 9/2006 | Falck, Jr. .................. A61B 3/16 600/406 |

OTHER PUBLICATIONS

International Search Report and Written Opinion dated Aug. 2, 2019 in corresponding International Patent Application No. PCT/US2019/033333, 11 pages.

Davanipour, Zoreh et al., "Ocular Tonometry and Sporadic Creutzfeldt—Jakob Disease (sCJD): A Confirmatory Case-Control Study", British Journal of Medicine and Medical Research, vol. 4, No. 12, pp. 2322-2233 (2014).

* cited by examiner

REPLACEABLE PRISM WITH FLEXIBLE TAB SYSTEM FOR APPLANATION TONOMETER, APPLANATION TONOMETER CONTAINING SAME, AND METHOD OF LOADING PRISM INTO APPLANATION TONOMETER

CROSS-REFERENCE TO PRIOR APPLICATIONS

This application is a National Stage of PCT/US2019/033333, filed May 21, 2019, and designating the United States (published on Nov. 28, 2019, as WO 2019/226662 A1), which claims priority under 35 U.S.C. § 119 to U.S. Provisional Application No. 62/674,768, filed May 22, 2018, each hereby expressly incorporated by reference in its entirety and each assigned to the assignee hereof.

TECHNICAL FIELD

An applanation tonometer is described for measuring intraocular pressure of the human eye. The applanation tonometer includes a replaceable prism designed for use with a single subject to block transmission of infectious diseases and protect public health. The tonometer also offers greater energy efficiency, improved optical performance, and more consistent prism insertion force when compared with conventional tonometers.

BACKGROUND

Tonometers are instruments used to measure intraocular pressure. There are three types of tonometers—indentation, air puff and applanation. Applanation tonometers are based the physical principle of the Imbert-Fick law where the pressure inside a sphere is equal to the force applied divided by the area flattened or applanated, i.e., Intraocular pressure=Contact force/Area of contact. Applanation tonometers measure the force required to flatten (or applanate) a constant area of the eye to determine the corresponding intraocular pressure. Indentation and air puff tonometers are not based on the Imbert—Fick law, and are thus, less accurate for measuring intraocular pressure. Additionally, air-puff tonometers aerosolize tears creating an inhalation hazard. (Micoraerosol Formation in Noncontact Air Puff Tonometry, *Arch. Ophthalmology*, vol. 109(2), pp. 225-28 (1991).) At this time, the Goldmann Tonometer is the most common device used to measure eye pressure. However, the Goldmann prism cannot be disinfected, as discussed in multiple technological publications. (Ocular Tonometry and Sporadic Creutzfel—Jacob Disease: A confirmatory Case Control Study, *Br. J. Med. Res.*, vol. 4(12), pp. 2322-33 (2014).) In fact, the prism in a Goldmann tonometer is not replaced, and is, instead, repeatedly with multiple subjects, which results in potential results in a serious contamination problem.

Figure 1:
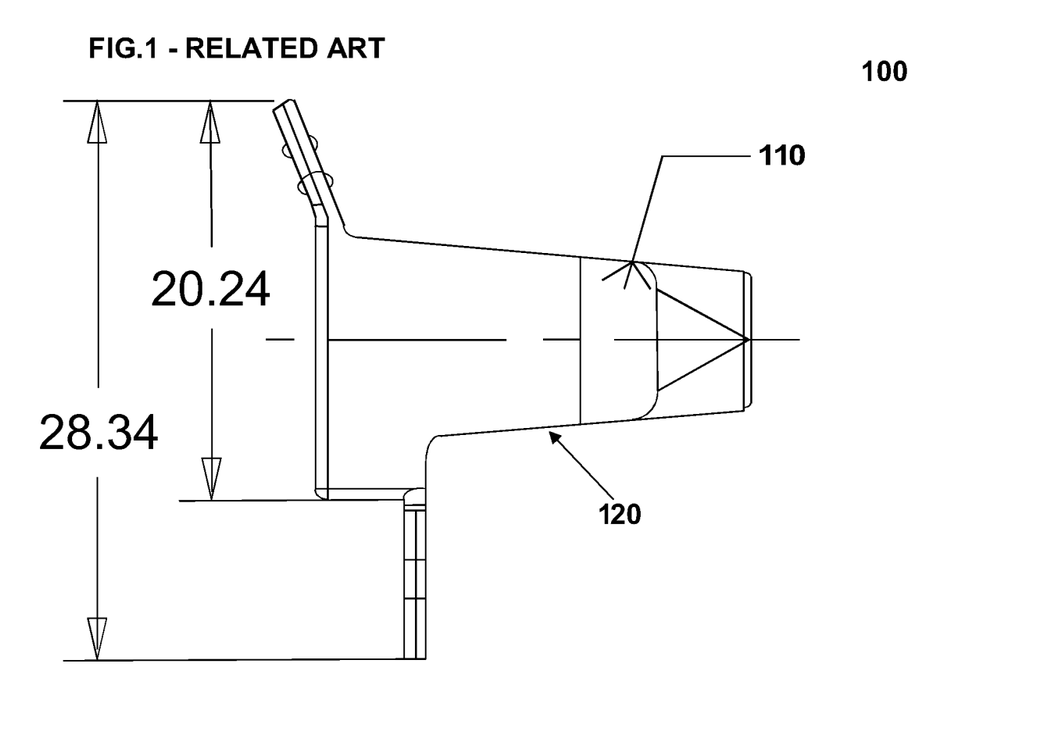
FIG. 1 is an illustration of a related art tonometer with a standard prism inserted therein.

Applanation tonometers are available in several forms, and they all, generally, include a replaceable prism. For example, U.S. Pat. No. 5,070,875 ("the '875 Patent") discloses an applanation tonometer having a replaceable prism, and U.S. Pat. No. 6,736,778 ("the '778 Patent") improves on the prism and its replacement, while otherwise relying on tonometer components such as described in the '875 patent. A standard set-up for an applanation tonometer 100 is illustrated in FIG. 1, where the prism 110 is manually inserted into a prism holder 120. However, existing applanation tonometers do not require the prisms to be replaced when measuring the intraocular pressure of multiple subjects, and are thus, problematic. Reusing the prism for multiples subjects can result in the spread of infectious diseases, causing a public health issue. Existing tonometers are also energy inefficient and offer less than optimal optical performance due to the manual insertion or placement of the prism with an inconsistent or variable insertion force.

Various new features of the replaceable prism described in this application address the above-discussed problems associated with applanation tonometers that use standard, manually-inserted and replaceable prisms.

SUMMARY

An inventive embodiment of this application is directed to an optical prism mounting system comprising: a prism comprising a flexible insertion tab system; and a prism holder comprising an insertion channel. The flexible insertion tab system comprises at least one spring or flex tab and at least one bendable or flexible tab. The spring tab is flexed as the prism moves along the insertion channel, and the flexible insertion tab system connects with the prism holder and snaps into a locked position at the end of the insertion channel. The prism and the prism holder can be separated after use by disengaging the flexible insertion tab system. The optical operating range of the optical prism is from about 0 ADC to about 600 ADC, which represents a significant improvement in energy efficiency over existing tonometers by at least about 50%.

In another inventive embodiment, the flexible insertion tab system and the prism holder each comprise a portion of an interlock that obstructs movement of the prism once the interlock is engaged.

In another inventive embodiment, the prism is configured for horizontal movement prior to engaging the interlock.

In another inventive embodiment, the portion of the interlock of the flexible insertion tab system and the portion of the interlock of the prism holder have oppositely angled surfaces, such that the oppositely angled surfaces are arranged to block any movement in a prism exit direction once mechanically engaged or placed into contact.

In another inventive embodiment, the prism holder further comprises a strain gauge.

In another inventive embodiment, the flexible tab system provides an improved insertion force, which is at least about 50% more consistent than a conventional manual insertion approach and when measured with a strain gauge. In exemplary embodiments, the insertion force of the prism is from about 0 ADC to about 768 ADC.

In another inventive embodiment, an initial insertion position of the prism is controlled by the configuration of the flexible insertion tab system.

In another inventive embodiment, the prism is designed to be dismounted after measuring an intraocular pressure of a single subject so that the prism cannot be reused with another subject.

In another inventive embodiment, optical light transmission of the prism is at least about 40% greater than optical light transmission of a prism in an optical prism mounting system that does not include a flexible insertion tab system.

In another inventive embodiment, the prism holder further comprises a microprocessor to regulate the maximum time for setting the tonometer.

In another inventive embodiment, the maximum time for setting the tonometer is not more than about 150 seconds.

In another inventive embodiment, the prism tab insertion force is at least about 50% more consistent than the prism tab insertion force of an optical prism mounting system that does not include the flexible insertion tab system. In another inventive embodiment, the optical prism mounting system further comprises a housing, such that the prism is operationally positioned in optical contact with or in proximity to a window of the housing.

In another inventive embodiment, the spring tab is located on a top back surface region of the prism.

In another inventive embodiment, the bendable tab located on a bottom internal surface of the prism.

In another inventive embodiment, the bendable tab is in contact with the strain gauge.

Yet another inventive embodiment of the subject application is directed to a method of mounting or inserting a prism in a tonometer. The method comprises: inserting the prism into one end of an insertion channel of a prism holder of the tonometer. The prism comprises a flexible insertion tab system comprising at least one spring tab; applying an initial force to the prism to move the prism along the insertion channel; activating a spring force of the spring tab of the prism at a transition point of the insertion channel; and locking the prism in place at an opposite end of the insertion channel. The optical operating range of the tonometer is from about 0 ADC to about 600 ADC, and the maximum time for setting the tonometer is not more than about 150 seconds.

In another inventive embodiment, the initial insertion force is applied by a user, but the subsequent force that causes the prism to be finally positioned in the tonometer is provided by the flexible tab system.

DETAILED DESCRIPTION

An inventive aspect of this application is a replaceable prism designed for use in an applanation tonometer. The prism of this application is designed for: (1) use with only a single subject, which blocks transmission of infectious diseases and protects public health; (2) providing improved optical performance; (3) providing more energy-efficient operating; and (4) providing more consistent insertion force than conventional, manual insertion prisms. In exemplary embodiments, the subject can be a mammal, including, but not limited to, a dog, a cat, a horse, a human, and the like. In exemplary embodiments, the subject is a human.

The optical system that the prism is a part of, has two functions: (1) imaging the eye; and (2) determining if the prism has been used previously. The optical system includes a strain gauge as part of the tonometer, and the interaction of the strain gauge and the prism determines if the prism has been used.

This is an important, inventive, and unexpectedly-superior aspect of this application, because existing tonometers pose a risk of infection from possible reuse with multiple patients. Lethal and non-lethal infectious agents are present in tears, and standard tonometers can allow for (even by mistake) reuse of the same prism multiples times for different subjects. This leads to an enhanced risk in transmission of lethal and non-lethal infectious diseases. The replaceable prism, and the corresponding optical system, of this application is designed to be used only for a single patient, which prevents or subsequently minimizes the possible transmission of infectious diseases and protects the public health.

Figure 2A:
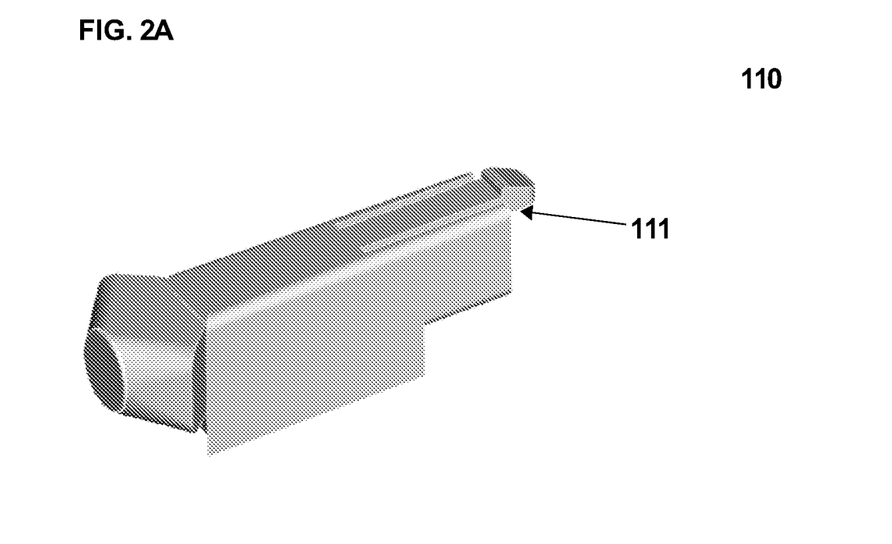
FIG. 2A is a side-view of a replaceable prism according to an embodiment of this application.
Figure 2B:
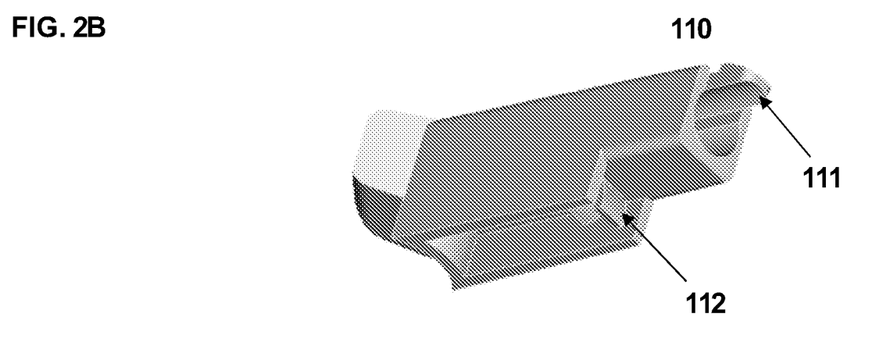
FIG. 2B is a bottom-view of a replaceable prism according to an embodiment of this application.

The prism of this application includes a flexible insertion tab system, which is housed in a channel or passageway leading to an operating face of the prism, and is designed for horizontal insertion into a prism holder of a tonometer. As illustrated in FIG. 2A and FIG. 2B, the flexible insertion tab system includes at least one spring tab 111, which can be molded onto the top back surface of the prism, and is designed to lock the prism into the prism holder. The spring tab can be made of any sufficiently flexible material including, for example, medical grade polymer materials, including but not limited to, polycarbonates, polyacrylates, polystyrenes, polybutadienes, and corresponding copolymers thereof.

Figure 3:
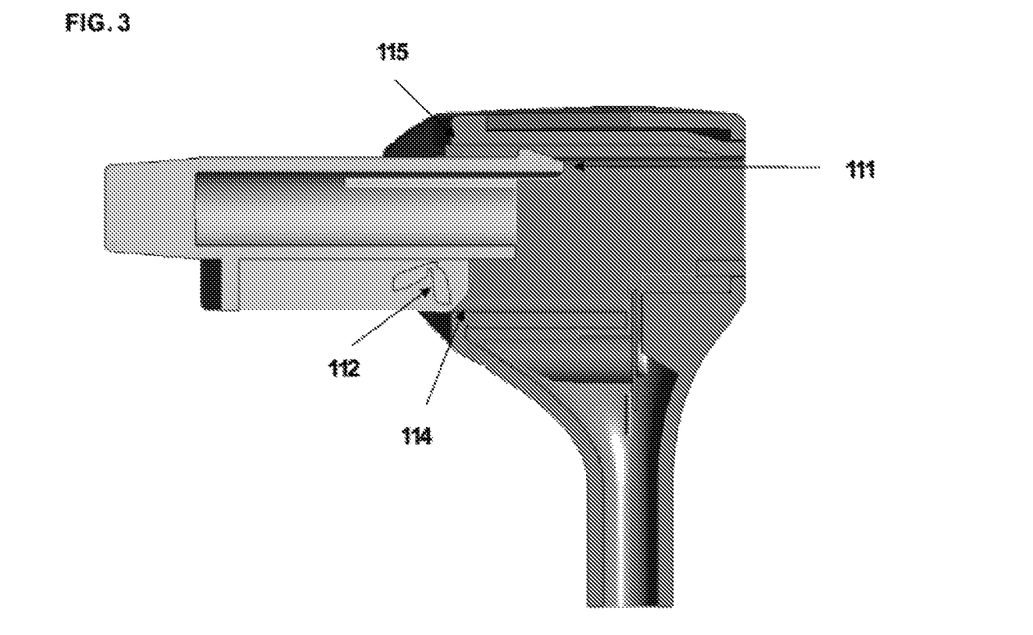
FIG. 3 is a side-view illustrating the insertion of a replaceable prism into a tonometer according to an embodiment of this application.

The spring tab secures the prism so that the optical surfaces of the prism are substantially aligned with the optical detector and the optical emitter of the tonometer. The spring tab also ensures that at least one bendable tab 112 located on the bottom internal surface of the prism contacts the strain gauge of the tonometer. The bendable tab can be made of any sufficiently bendable material such as, for example, one or more materials selected from the group consisting of polycarbonates, polyacrylates, polystyrenes, polybutadienes, combinations thereof and the like. As further illustrated in FIG. 3, the optical system includes a clearance 113 for the spring tab 111 and a lead-in 114 for inserting the prism into the tonometer. The spring tab flexes upon application of a force, whereas the bendable tab bends upon application of a force. The material of spring tab and the bendable tab may be the same or different, and includes, but is not limited to, medical grade polymer materials, such as polycarbonates, polyacrylates, polystyrenes, polybutadienes, and corresponding copolymers thereof.

The interaction of the strain gauge, which is a custom component, and the prism determines if the prism has been used. When the bendable tab interacts with the prism it is bent or relieved on a hinge. The strain gauge records this bending force. Once the tab has been bent, less force is required to bend it a second time, i.e., the bendable tab is structurally altered. Thus, the strain gauge can determine that the prism has been used by detecting a reduction in the force required to bend the tab. This method is an economical option to ensure that a prism cannot be reused. This method is not limiting, and other methods, including but not limited to, demagnetizing a magnetic strip on a prism during insertion, using an actinic method, altering a chemical placed on the prism on exposure to light, having a tab on the prism which engages a microswitch in the tonometer, having a tab that is mechanically altered so the prism cannot be reinstated, and the like, can be used to determine whether a prism has been used.

Figure 4A:
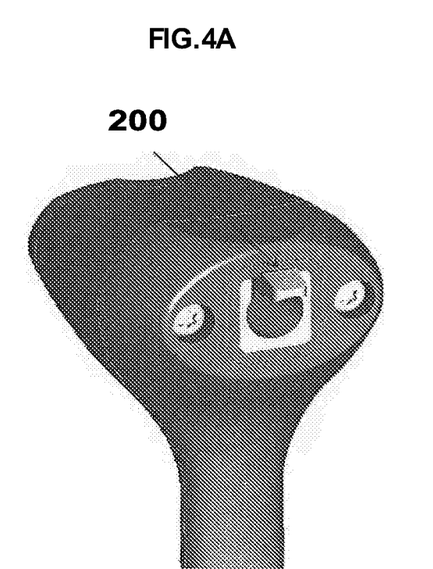
FIG. 4A is a back-view of a tonometer after a replaceable prim is inserted therein according to an embodiment of this application.
Figure 4B:
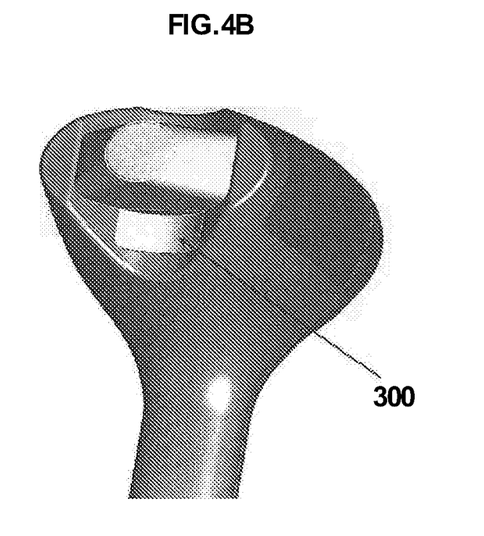
FIG. 4B is a front-view of a tonometer after the replaceable prim is inserted therein according to an embodiment of this application.

When the tonometer is to be used, the spring tab of the prism is pushed by a user toward the operating position. A concave area is located on the front bottom surface of the prism for a user to push the prism into the first one-third of the holder. The insertion force on the prism is provided by the user during an initial movement of the prism so as not to exceed a distance or force applied. This also flexes the spring tab as the prism moves along an early part of its travel, and the energy generated by the movement of the prism is stored as spring energy. When the spring tab reaches a transition point, the prism can continue along the insertion path to completion by virtue of the stored spring force. At that point, the flexible insertion tab snaps into a locked position. As illustrated in FIG. 4A and FIG. 4B, the spring tab snaps the prism into place inside the tonometer (200) and the tonometer contains a plurality of rails (300) protecting the bendable tab, which are located on the bottom surface of the prism. The plurality of rails guide the prism into the prism holder and ensure that the bendable tab is only bent by the strain gauge. After the intraocular pressure is measured, the prism is ejected from the prism holder by, for example, pressing the spring tab downward or otherwise disengaging it to allow for ejection.

The above-described process of inserting the prism into the tonometer has several advantages. First, this process ensures that every time a prism is loaded into the tonometer, the final operating position of the prism is substantially controlled by the configuration of the flexible insertion tab system. The movement of the prism is independent of the initial operator force used to initiate movement of the prism. Instead, the movement of the prism is controlled by the spring tab and the spring force stored therein. As a result, the insertion of the prism in the tonometer described herein is consistent. This is an advantage over prior art systems in which the prism is inserted solely using operator force. Additionally, the prism is not forced toward the operating position by accidental application of force by a user. Second, the ability of the flexible insertion tab system to move the prism into a locked position ensures that the prism is operationally poised in optical contact with and/or proximity to a window of the housing. As a result, insertion inaccuracies are eliminated or substantially minimized, i.e., the prism can be positioned at the final operating position accurately for each successive use. That is, the insertion force is more consistent and reproduceable. This also unexpectedly increases the accuracy and/or optical performance of the signals measured by the tonometer based on the contact of the eye with the prism compared to previously-known tonometers that do not employ the flexible tab system.

Once a prism is inserted into the tonometer, it can be used for an applanation reading as many times as desired on a single subject. Thereafter, the prism is made inoperable on another subject by having an onboard microprocessor, and designating the maximum time for operating the tonometer to about 150 seconds, preferably about 140 seconds, about 130 seconds, about 120 seconds, about 110 seconds, about 100 seconds, about 90 seconds, about 80 seconds, about 70 seconds, about 60 seconds, about 50 seconds, about 40 seconds, about 30 seconds, about 20 seconds, about 10 seconds, and the like. The microprocessor present in the tonometer tracks the time from which the last measurement and/or contact with the eye has occurred. If a measurement and/or contact with the eye has occurred and the maximum allowable time has elapsed, the tonometer will prompt for an unused new prism to be inserted before another measurement can be attempted. This bars any further use of the prism for a period of not more than about 150 seconds, which is insufficient time to change to another subject and/or another slit lamp microscope, because the tonometer cannot be deployed within this time. Thus, this system avoids transmission of contaminated material between patients.

Furthermore, the optical detector of this application is designed to operate in a range of about 0 to about 1024 analog to digital counts (ADC). The optical operating range is measured by the optical detector, which is part of the tonometer. In standard devices, a microprocessor monitors and records the detector output, and the sensitivity of the detector is decreased when the optical system operates around an average value of about 0 to about 200 ADC due to an inefficient prism design, which significantly impairs measurement sensitivity. With the new prism design, the upper limit of the average sensitivity measurement increases from about 200 to about 600 ADC, which also results in an increase in the accuracy of the measurements. The standard optical detectors generally operate in a range of about 0 to about 200 ADC due to an inefficient prism design, which significantly impairs measurement sensitivity. With the new prism design described in this application, the optical operating range increases from about 0 to at least about 600 ADC, which unexpectedly, and significantly, increases optical sensitivity and accuracy of the intraocular pressure measurements by ≥about 50%, preferably by ≥about 60%, ≥about 70%, about 80%, ≥about 90%, and the like, and increases the light transmittance by ≥about 40%, preferably ≥about 50%, ≥about 60%, ≥about 70%, ≥about 80%, ≥about 90%, and the like. With the new prism design, the maximum optical sensitivity shifts from a lower-end to a mid-range of the optical detector.

Strain Gauge Detectors generally operate in a range of about 0 to about 1024 ADC. With the standard prism design the detection range was limited to from about 0 to about 512 ADC. The insertion force is measured by the strain gauge when a prism is inserted, and the force is monitored and recorded by the microprocessor present in the tonometer. The average optimal operating range of the strain gauge is about 700 ADC. However, with the new prism design of this application, the detection range increases to from about 0 to about 800 ADC, preferably from about 0 to about 700 ADC, from about 0 to about 600 ADC, and the like. More preferably, the detection range increases to from about 0 to about 786 ADC. Because the strain gauge measurement is used to determine whether the prism has already been used, the narrow detection range of standard prism systems resulted in significant false detection rates. However, the broader detection range possible with the new prism design of this application results in a significant reduction in the false detection rates.

Further, compared to standard tonometers, the optical feedback of the tonomoters using the replaceable prisms of the subject application consistently reached saturation at range of about 136 to about 139 DAC at a significantly reduced LED driving voltage compared to from about 90 to about 115 DAC of the standard tonometers. The LED output was reduced to about 110 from about 140 DAC for standard tonometers, and the photodetector bias was increased to about 135 from about 115 DAC. The readings were mechanically consistent over multiple prisms that were tested. Representative test data for the tonometers of this application are shown in Table 1, and representative test data for standard tonometers are shown in Table 2.

The average values for five sample batches of from cavity 1 through cavity 8 of an eight-cavity mold for the prism described in this application are represented as Examples 1 to 5 in Table 1 below. In Table 2 below are the test results of prisms from a previous design. These comparative sample results labeled Comparative Example 1 through Comparative Example 8 represent a random sample of 1% of 4000 prisms manufactured from an eight-cavity mold. The average values of the five prisms from each cavity is presented in Table 2. The prisms were tested using 2 different light intensity levels, one at 125 DAC (high) and the other at 110 DAC (low). The prisms were tested using a production photo detector, an LED emitter and a circuit board.

In comparing the results of testing of the prism described in this application as compared to the previous design, the strain gauge and photo-detector performance is more consistent. The enhanced strain gauge performance decreases the probability of a contaminated prism being used on a different individual. The improved photo-detector performance increases measurement sensitivity, accuracy and precision. The improved alignment of the prism, due to the flexible tab, with the emitter and detector allows the system to use less emitter driving voltage which increases the device efficiency rating.

TABLE 1

| | Strain Gauge Output in grams | Feedback Detector DAC Value | Emitter DAC Value | Photodetector DAC Cal Value |
|---|---|---|---|---|
| Example 1 | 359.25 | 138 | 110 | 135 |
| Example 2 | 357.38 | 138.25 | 110 | 135 |
| Example 3 | 359.63 | 137.50 | 110 | 135 |
| Example 4 | 359.63 | 138.5 | 110 | 135 |
| Example 5 | 361.88 | 138.25 | 110 | 135 |

TABLE 2

| | Strain Gauge Output in grams | Emitter High DAC Output 1024 MAX = 5 volts | Photo Detector Feedback (High) | Emitter Low DAC Output 1024 MAX = 5 volts | Photo Detector Feedback (Low) | Detector ADC Value 1025 MAX = 5 volts |
|---|---|---|---|---|---|---|
| Comparative Example 1 | 218 | 125 | 898.6 | 110 | 435.8 | 115 |
| Comparative Example 2 | 231.2 | 125 | 872.2 | 110 | 354 | 115 |
| Comparative Example 3 | 244.4 | 125 | 781.6 | 110 | 319 | 115 |
| Comparative Example 4 | 257.4 | 125 | 826.8 | 110 | 398 | 115 |
| Comparative Example 5 | 270.6 | 125 | 1021.2 | 110 | 896.4 | 115 |
| Comparative Example 6 | 283.8 | 125 | 939.6 | 110 | 491.2 | 115 |
| Comparative Example 7 | 297 | 125 | 1010 | 110 | 608.2 | 115 |
| Comparative Example 8 | 310 | 125 | 811 | 110 | 384.2 | 115 |

Although exemplary embodiments of the present disclosure have been described in detail with reference to the accompanying drawings, the present disclosure is not limited thereto and may be embodied in many different forms without departing from the technical concept of the present disclosure. Therefore, the exemplary embodiments of the present disclosure are provided for illustrative purposes only and are not intended to limit the technical concept of the present disclosure. The protective scope of the present disclosure should be construed based on any appended claims and combinations thereof, and all the technical concepts in the equivalent scope thereof should be construed as falling within the scope of the present disclosure. As various changes could be made in the above methods and compositions without departing from the scope of the invention, it is intended that all matter contained in the above description shall be interpreted as illustrative and not in a limiting sense. Other embodiments within the scope of the claims herein will be apparent to one skilled in the art from consideration of the specification or practice of the invention as disclosed herein. It is intended that the specification be considered exemplary only, with the scope and spirit of the invention being indicated by the claims.

Moreover, certain features of the disclosure may be utilized independently of the use of other features, all as would be apparent to one skilled in the art after having the benefit of this description of the disclosure. Expressions such as "including", "comprising", "incorporating", "consisting of", "have", "is" used to describe and claim the present disclosure are intended to be construed in a non-exclusive manner, namely allowing for items, components or elements not explicitly described also to be present. Reference to the singular is also to be construed to relate to the plural. Reference to "about" or "approximately" is to be construed to mean plus or minus 20%. Similarly, reference to any percentage of an additive is construed to mean plus or minus 20%.

Further, various embodiments disclosed herein are to be taken in the illustrative and explanatory sense, and should in no way be construed as limiting of the present disclosure. All joinder references (e.g., attached, affixed, coupled, connected, and the like) are only used to aid the reader's understanding of the present disclosure, and may not create limitations, particularly as to the position, orientation, or use of the systems and/or methods disclosed herein. Therefore, joinder references, if any, are to be construed broadly. Moreover, such joinder references do not necessarily infer that two elements are directly connected to each other.

Additionally, all numerical terms, such as, but not limited to, "first", "second", "third", "primary", "secondary", "main" or any other ordinary and/or numerical terms, should also be taken only as identifiers, to assist the reader's understanding of the various elements, embodiments, variations and/or modifications of the present disclosure, and may not create any limitations, particularly as to the order, or preference, of any element, embodiment, variation and/or modification relative to, or over, another element, embodiment, variation and/or modification.

It will also be appreciated that one or more of the elements depicted in the drawings/figures can also be implemented in a more separated or integrated manner, or even removed or rendered as inoperable in certain cases, as is useful in accordance with a particular application.

What is claimed is:

1. An optical prism mounting system comprising:
a prism comprising a flexible insertion tab system; and
a prism holder comprising an insertion channel;
wherein the flexible insertion tab system comprises at least one spring tab and at least one bendable tab;
wherein the at least one spring tab is flexed as the prism moves along the insertion channel;
wherein the flexible insertion tab system connects with the prism holder and snaps into a locked position at the end of the insertion channel;
wherein the prism and the prism holder can be separated after use by disengaging the flexible insertion tab system, and
wherein an optical operating range of the optical prism is from about 0 ADC to about 600 ADC.

2. The optical prism mounting system according to claim 1,
wherein the flexible insertion tab system and the prism holder each have a portion of an interlock that obstructs movement of the prism once the interlock is engaged.

3. The optical prism mounting system according to claim 2,
wherein the prism and the prism holder are configured for horizontal movement prior to engaging the interlock.

4. The optical prism mounting system according to claim 2,
wherein the portion of the interlock of the flexible insertion tab system and the portion of the interlock of the prism holder have oppositely angled surfaces, such that the oppositely angled surfaces are arranged to block any movement in a prism exit direction.

5. The optical prism mounting system according to claim 1, wherein the prism holder further comprises a strain gauge.

6. The optical prism mounting system according to claim 5, wherein a strain gauge detection range of the insertion force of the prism is from about 0 ADC to about 768 ADC.

7. The optical prism mounting system according to claim 1, wherein an initial insertion position of the prism is controlled by the configuration of the flexible insertion tab system.

8. The optical prism mounting system according to claim 1, wherein the prism is dismounted after measuring an intraocular pressure of a single subject.

9. The optical prism mounting system according to claim 1, wherein optical light transmission is at least about 40% than optical light transmission of a prism in an optical prism mounting system that does not include a flexible insertion tab system.

10. The optical prism mount system according to claim 1, wherein the prism holder further comprises a microprocessor to regulate the maximum time for setting the tonometer.

11. The optical prism mounting system according to claim 1, wherein the maximum time for setting the tonometer is about 150 seconds.

12. The optical prism mounting system according to claim 1, wherein a prism insertion force is at least about 50% than a prism insertion force of an optical prism mounting system that does not include the flexible insertion tab system.

13. The optical prism mounting system according to claim 1, further comprising a housing, such that the prism is operationally positioned in optical contact with a window of the housing.

14. The optical prism mounting system according to claim 1, wherein the at least one spring tab is located on a top back surface of the prism.

15. The optical prism mounting system according to claim 1, wherein the at least one bendable tab is located on a bottom internal surface of the prism.

16. The optical prism mounting system according to claim 5, wherein the at least one bendable tab is in contact with the strain gauge.

17. The optical prism mounting system according to claim 1, wherein the prism further comprises a plurality of rails located on a bottom surface of the prism.

18. The optical prism mount system according to claim 17, wherein the plurality of rails protects the at least one bendable tab.

19. A method of mounting a prism in a tonometer, the method comprising:
inserting the prism into one end of an insertion channel of a prism holder of the tonometer, wherein the prism comprises a flexible insertion tab system comprising at least one spring tab;
applying an initial force to the prism to move the prism along the insertion channel;
activating a spring force of the at least one spring tab of the prism at a transition point of the insertion channel; and
locking the prism in place at an opposite end of the insertion channel,
wherein an optical operating range of the tonometer is from about 0 ADC to about 600 ADC, and
wherein the maximum time for setting the tonometer is about 150 seconds.

20. The method according to claim 19, wherein the initial force is applied by a user.

21. The method according to claim 19, wherein the flexible insertion tab system and the prism holder each have a portion of an interlock that obstructs movement of the prism once the interlock is engaged.

22. The method according to claim 19, wherein the portion of the interlock of the flexible insertion tab and the portion of the interlock of the prism holder have oppositely angled surfaces to lock the prism in place at the opposite end of the insertion channel.

23. The method according to claim 19, wherein a strain gauge detection range of the insertion force of the prism is from about 0 ADC to about 768 ADC.

24. The method according to claim 19, wherein an initial insertion position of the prism is controlled by the configuration of the flexible insertion tab system.

25. The method according to claim 19, wherein the prism is dismounted after measuring intraocular pressure of a single subject.

26. The method according to claim 19, wherein optical light transmission is at least about 40%≥optical light transmission of a prism in an optical prism mounting system that does not include a flexible insertion tab.

27. The method according to claim 19, wherein a prism tab bending force is about 50% a prism tab bending force of an optical prism mounting system that does not include the flexible insertion tab system.

28. The method according to claim 19, wherein the tonometer further comprises a housing, and the prism is operationally positioned in optical contact with a window of the housing.

29. The method according to claim 19, wherein the at least one spring tab is located on a top back surface of the prism.

30. The method according to claim 19, wherein the prism further comprises at least one bendable tab located on a bottom internal surface of the prism.

31. The method according to claim 30, wherein the at least one bendable tab is in contact with a strain gauge.

32. The method according to claim 19, wherein a strain gauge detection range of the insertion force of the prism is from about 0 ADC to about 768 ADC.

33. The method according to claim 19, wherein the prism further comprises a plurality of rails located on a bottom surface of the prism.

34. The method according to claim 33, wherein the plurality of rails protects the at least one bendable tab.

* * * * *